United States Patent [19]

Giacobbe

[11] 4,031,100

[45] June 21, 1977

[54] PROCESS FOR MAKING 2,6-DIFLUOROPYRIDINE

[75] Inventor: Thomas J. Giacobbe, Concord, Calif.

[73] Assignee: The Dow Chemical Company, Midland, Mich.

[22] Filed: Aug. 23, 1976

[21] Appl. No.: 716,863

[52] U.S. Cl. .......................................... 260/290 HL
[51] Int. Cl.² ...................................... C07D 213/81
[58] Field of Search ............................. 260/290 HL

[56] References Cited

UNITED STATES PATENTS 3,629,424  12/1971  Torba ................................ 424/263

FOREIGN PATENTS OR APPLICATIONS 1,306,517  2/1973  United Kingdom ......... 260/290 HL

*Primary Examiner*—Alan L. Rotman

*Attorney, Agent, or Firm*—Robert R. Stringham

[57] ABSTRACT

It has been found that practical reaction rates can be attained without resort to the high temperatures previously employed in the preparation of 2,6-difluoropyridine from the corresponding dichloropyridine and KF, if:

a. dimethyl sulfoxide is employed as the reaction medium;
b. the reaction mixture contains solid KF particles and dissolved tetramethyl ammonium or phosphonium chloride;
c. there is present in the reaction mixture less than 0.1 grams of acids, bases or organic hydroxy compounds and less than 1.0 grams of water, per 100 grams of solvent, and
d. the reaction mixture is intensely stirred.

17 Claims, No Drawings

PROCESS FOR MAKING 2,6-DIFLUOROPYRIDINE

BACKGROUND OF THE INVENTION

British Pat. No. 1,306,517 discloses a process for converting chloropyridines to fluoropyridines by reaction with alkali metal fluorides in polar, aprotic solvents at temperatures of from 160° to 250° C. The solvent may or may not be mixed with water and the reaction is carried out in the presence of an acid, base or organic hydroxy compound as an "initiator". The preferred solvent is sulfolane (tetramethylene sulfone) and the preferred initiator is ethylene glycol.

In the sole example in the patent of 2,6-difluoropyridine preparation, a 62% conversion of 2,6-dichloropyridine to the difluoro derivative is reported as having been obtained by refluxing a mixture of about 2 moles of the dichloropyridine and about 8 moles of anhydrous KF in sulfolane (containing 1.2 weight percent of ethylene glycol) for 2 hours at 225°–235° C.

Reaction temperatures as high as 225° and are not particularly attractive for 2,6-difluoropyridine production. The boiling point of the latter compound is only about 125° at sea level and it is therefore necessary either to operate under a pressure at least equal to the (quite substantial) autogenous pressure of the reaction mixture or to allow the difluoro compound to distil out of the reaction mixture as formed and to provide for reflux return to avoid losses of the chloro/fluoro intermediate, which is also quite volatile. However, substantially lower reaction rates can be anticipated at lower temperatures. In fact, a reaction period of 25–30 hours is required to attain an 80% yield of the difluoropyridine at 150°, in DMSO, and much longer periods are required in other solvents, including sulfolane, at this temperature.

The use of DMSO as the reaction medium at higher temperatures is contraindicated by two considerations: (1) the solubility of KF in this solvent goes down, rather than up, as the temperature increases (see Table 1); and (2) DMSO is known (Traynelis et al., *J. Org. Chem.*, 29, 221 (1964)) to slowly decompose at reflux temperature (~189° C.) and (according to Finger and Starr, *J.A.C.S.*, 81, 2674 (1959)) to react with halogen compounds. Substantial alteration of DMSO would then be expected at elevated temperatures in the presence of such inherently reactive compounds as 2,6-difluoro- or 2-chloro-6-fluoropyridine.

On the other hand, if the reaction period could be sufficiently shortened by use of an appropriate catalyst, an unacceptable degree of solvent decompositioned might not result. According to the British Pat. No. 1,306,517 patent, ethylene glycol is the "initiator" of choice. Therefore, despite the fact that ethylene glycol is known (Traynelis at al., loc. cit.) to promote alteration of DMSO, an attempt has been made to employ the glycol as a catalyst for the reaction of 2,6-dichloropyridine with KF in DMSO at 186° C. 74.35 and 13.3% yields, respectively, of the difluoro and chloro/fluoro products were attained in a reaction period of 5.5 hours. However, a total of about 11% of the dichloropyridine was found to have been converted to undesired, solvent-derived byproducts. Accordingly, the use of such catalysts as ethylene glycol appears to be ruled out.

It is known that replacement of chloro substituents on aromatic rings by fluorine can be achieved at less elevated temperatures if the ring is also substituted with an activating group. Thus, Finger and Kruse reported (*J.A.C.S.*, 78, 6034 (1956)) that a 47% yield of a monofluoro derivative was obtained by reacting 2,4-dichloronitrobenzene with excess KF in DMSO (dimethyl sulfoxide) at 180° for 6 hours; they attributed this result to activation by the nitro group. Similarly, U.S. Pat. No. 3,629,424 discloses (Example 5) that 30 grams (a 34.7% yield) of 3,5-dichloro-2,6-difluoro-4-cyanopyridine was obtained by reacting 100 grams of tetrachloro-4-cyanopyridine in DMSO at 40°–50° for 5 hours. However, no way of introducing a subsequently removable activating group in 2,6-dichlorpyridine is evident.

It is evident that it would be highly desirable if a method could be found whereby the reaction of KF and chlorine substituents alpha to the ring nitrogen, in pyridine compounds lacking activating substituents, could be made to proceed at more practical rates at temperatures at which solvents such as DMSO are stable to 2,6-difluoro- and 2-chloro-6-fluoropyridine. In other words, a more effective catalyst for the reaction than the "initiators" disclosed in the British Pat. No. 1,306,517 patent is needed.

Certain so-called "crown ethers" have been reported to solubilize potassium fluoride in organic solvents, by solvating the $K^+$ ion, the $F^-$ ion accompanying the solvated cation as a closely associated counter ion. However, it has been found that crown ethers are of little value as catalysts for the fluoride/chloride exchange reaction at point.

Since the solubility of KF is generally low, the exchange reaction is essentially a heterophase reaction and a technique of catalysis appropriate to such reactions is indicated. In recent years, so-called "phase-transfer" catalysis has proven to be an effective technique for facilitating a variety of heterophase reactions. According to a cursory review of this type of catalysis included in *Eastman Organic Chemical Bulletin*, Vol. 48, No. 1, 1976, quaternary ammonium (and phosphonium) salts have been found to be excellent phase transfer catalysts.

The vast majority of applications of phase-transfer catalysis described in the literature involve transfer of reactive species between two liquid phases, one of which is usually aqueous. However, an example of transfer between a solid phase and an organic liquid phase has been disclosed. Huang and Dauerman reported (*Industrial and Engineering Chemistry, Product Research and Development*; Vol. 8, No. 3, Sept. 1969, pp. 227–232) the use of various amines and triphenyl phosphine as catalysts for anhydrous acetylations of certain aralkyl and alkyl chlorides with sodium acetate in the presence or absence of organic solvents.

Similarly, Wagenknecht et al. reported (*Synthetic Communications*, 2(4), 215–19 (1972)) that ester formation is further facilitated if the alkyl halide is reacted with a solution or suspension of a preformed, hydrated quaternary ammonium carboxylate in a non-hydroxylic solvent (rather than with a metal carboxylate in the presence of an amine or ammonium salt). Similar results were obtained when the anion in the preformed salt was a phenolate or nitrate ion.

Tetraalkyl ammonium fluorides have been used to effect nucleophilic displacement of tosylate groups (in tosylated sugars or hydroxy acids) by fluoride, according to Birdsall, *Tetrahedron Letters* No. 28, pp. 2675–2678, 1971. There are not heterophase reactions and do not involve phase transfer catalysis. Further-more, Birdsall reported formation of unsaturated (dehydrofluorinated) acid by-products in yields of from 30 to 100 percent, depending on the basicity of the solvent used, when tetrabutyl ammonium fluoride was employed as the fluoride source material.

The undesired formation of dehydrofluorinated acids experienced by Birdsall may be attributable to the strong tendency of fluoride ions to abstract protons from organic substrates in the presence of solvents such as DMSO. In view of the latter tendency and the fact the high charge density of the small fluoride ion makes it more difficult to solubilize than larger anions such as carboxyl, phenolate or nitrate, it could not be anticipated with confidence that quaternary ammonium or phosphonium chlorides would effectively catalyze the hetero-phase exchange reaction between KF and 2,6-dichloro- or 2-chloro-6-fluoropyridine.

OBJECTS OF THE INVENTION

A primary object of the present invention is to provide a catalyst for the heterophase exchange reaction of KF and chloropyridines which is effective at temperature substantially below 225° C.

It is also an object of the present invention to provide an improvement in the method of making 2,6-difluoropyridine by reacting KF and 2,6-dichloro- or 2-chloro-6-fluoropyridine in aprotic, polar solvents, whereby practical reaction rates can be attained at temperatures well below those at which solvents such as DMSO tend to undergo alteration.

A further object is to provide a process for making 2,6-difluoropyridine from KF and 2,6-dichloro- or 2-chloro-6-fluoropyridine wherein the inclusion in the reaction mixture of materials which constitute a recovery or disposal problem, such as acids, bases and organic hydroxyl compounds, is avoided.

Yet another object is to provide a process of the preceding type which avoids or mitigates the corrosion problems inherent in the use of KF solutions at elevated temperatures.

SUMMARY OF THE INVENTION

The present invention is an improved process for making 2,6-difluoropyridine from 2,6-dichloro- or 2-chloro-6-fluoropyridine and alkali metal fluorides.

It has now been found that quaternary ammonium or phosphonium chlorides can be effectively utilized as catalysts for the foregoing exchange reaction, provided that none of the alkyl (or other organo) radicals in the quaternary chloride are other than methyl and the reaction mixture is intensely stirred.

More specifically, the invention is the improvement in the process of preparing 2,6-difluoropyridine by reaction KF with 2,6-dichloro- or 2-chloro-6-fluoropyridine at an elevated temperature in an aprotic, polar solvent, whereby practical reaction rates are attained without resort to temperature substantially above 185°, said improvement comprising:
 a. providing a mixture of solid KF particles and a solution, in DMSO, of:
  1. the alpha-chloropyridine reactant,
  2. a catalytically effective amount of a catalyst which is $(CH_3)_4N^+Cl^-$, $(CH_3)_4P^+Cl^-$ or both; said mixture containing less than 0.1 grams of acids, bases or organic hydroxy compounds and less than 1 gram of water, per 100 grams of DMSO, and
 b. intensely stirring said mixture and maintaining it at a temperature within the range of from about 100° to about 185° C.,
the reaction being carried out under an inert atmosphere if a reaction temperature above about 180° is employed.

The meaning to be given the term "intensely stirring" in the foregoing definition (and in the claims appended to these specifications) is that the reaction mixture is stirred with sufficient vigor so that the distribution of the solid KF particles in the mixture is essentially uniform. That is, the amount of particulated KF present in any unit volume of the reaction mixture will be within the range of 95–105% of the amount present in any other unit volume. Methods of ensuring that an essentially uniform distribution is maintained are discussed subsequently herein.

Advantageously, a reaction temperature of 180° or less is employed and it is highly desirable to use an inert gas pad at temperatures in the range of about 175° to about 185°.

In a preferred embodiment of the invention, the reaction temperature is within the range of from about 140° to about 175°, a more preferred range being from about 145° to about 170° C. The range from about 150° to about 165° is particularly preferred.

The preferred quaternary chloride for the practice of the invention is tetramethyl ammonium chloride (TMAC).

Preferred stirring rates are at least 50 rpm is baffled reaction vessels and at least 300 rpm is unbaffled reaction vessels, using a blade or impeller type stirrer.

Preferred overall KF to chloro-pyridine ratios in the reaction mixture are such as to provide from about 110 to about 125% of the stoichiometric requirement of KF for complete conversion of the 2,6-dichloro- and/or 2-chloro-6-fluoropyridine to 2,6-difluoropyridine.

The tetramethyl ammonium or phosphonium chloride catalyst is preferably employed in an amount of from about 0.3 to about 0.6 moles per mole of the dihalopyridine reactant present in the reaction mixture.

Preferred initial concentration of 2,6-dichloro- or 2-chloro-6-fluoropyridine in the solution (the liquid phase of the starting mixture) are within the range of from about 2 to about 3 moles per liter of solution.

DETAILED DESCRIPTION

It is critical to the attainment of practical reaction rates that the solvent employed as the reaction medium be DMSO. It is not known to what extent properties other than relative basicity and solvent ability are involved, but it has been found that the rate at which chlorine substituents in the 2 and 6 positions on pyridine rings are replaced by KF-derived fluorines is dependent on the solvent employed. In one instances, for example, the rate in DMSO was about 2.7 times the rate in sulfolane.

It is evident from the following tabulation that the solubility of KF in DMSO is quite low at ordinary ambient temperature and is several fold lower at elevated temperatures.

TABLE I

| KF Solubility in DMSO Temperature | Grams KF/100 Grams DMSO |
| --- | --- |
| 24° C. | 0.043 |
| 55 | 0.043 |
| 102 | 0.021 |
| 125 | 0.015 |

TABLE I-continued

| KF Solubility in DMSO | |
|---|---|
| Temperature | Grams KF/100 Grams DMSO |
| 150 | 0.013 |

This, DMSO would appear to be a poor choice as the medium for a reaction which requires elevated temperatures, even if a catalyst is to be employed. However, it has been found that solubility of KF as such is not controlling in the presence of tetramethyl ammonium or phosphonium chloride. That is, the rate of conversion of KF is much higher when $F^-$ enters the liquid phase through an exchange reaction across the interface between the solid KF particles and the dissolved quaternary chloride salt. (It is not known to what extent the catalyst affects the rates of conversion of the alpha-chloropyridine reactants, other than by increasing the $F^-$ activity in the liquid phase.)

The reaction mixture does not have to be anhydrous and it is convenient to be able to use DMSO containing the amount of water (up to about 0.2%) commonly present in the reagent grade solvent. Water contents in the reaction mixture of up to about 1 weight percent of the amount of DMSO present can be tolerated, at least in short term operations where corrosion is less of a concern. However, it is generally preferably that the reaction mixture contains 0.3 grams or less of water per 100 grams of DMSO. Water contents in the solvent of less than about 0.2% can be attained by drying over molecular sieves, by adding benzene and boiling off a water-benzene azeotrope or simply by distilling off a fore cut (under reduced pressure) until the pot temperature is above the boiling point of DMSO at that pressure.

The amount of DMSO used should be sufficient to ensure facile stirring but is not otherwise critical. DMSO to dihalopyridine mole ratios of less than about 3-3.5 to 1 result in reaction mixtures (slurries) which are difficult to stir. A ratio within the range of about 4 to about 6 to 1 is preferred and corresponds to a concentration range of from about 3 to about 2 moles per liter of solution, respectively. Ratios up to 10 to 1, or even higher, may be employed but confer no advantage and are uneconomic.

The amount of KF introduced to the reaction mixture should be at least sufficient to provide the stoichiometric requirement of fluoride for the reaction, assuming complete conversion of the dichloro- or fluoro-chloro pyridine starting material to 2,6-difluoropyridine is desired. Although KF is not very soluble, the mole ratio of undissolved (or total) KF to the dihalopyridine in the reaction mixture is significant (together with average particle size) in determining the KF surface area exposed to contact by the dissolved quaternary chloride. It is evident from the observed differences in reaction rates with and without intense stirring that the absolute rate of exchange of fluoride and chloride ions between the solid and liquid phases can be limiting upon the rate of exchange within the liquid phase. For this reason, it is beneficial to employ an excess of (finely comminuted) KF over the stoichiometric amount. On the other hand, as the amount of KF is increased, the amount of liquid phase required to avoid excessive stirring power requirements will also increase, so that the advantage of an excess of KF is, in effect, self-limiting. In general, an amount of KF equal to about 110-150 percent of the stoichiometric requirement will be satisfactory. Amounts equivalent to 250% or more of the stoichiometric amount may be used but little or no advantage is realized by going beyond an excess of about 50% over the stoichiometric quantity (100%).

It is essential to the full realization of the advantages of the present invention that the KF employed be of at least reagent grade. Where lower quality KF is used, substantial decreases in yield result.

Also, the reaction mixture should not contain more than about 0.1 gram (total) of acids, bases or organic hydroxy compounds per 100 grams of solvent, as these materials tend to result in lower reaction rates and/or to promote formation of undesired pyridine derivatives in which one or both of the halo substituents have been replaced with other groups.

It is critical to the attainment of practical reaction rates, in DMSO and at temperatures of 185° of less, that at least a catalytically effective amount of tetramethyl ammonium or phosphonium chloride be present in the liquid phase. The latter two salts are unique among quaternary onium halides as catalysts for the reaction between KF and 2,6-dichloro- or 2-chloro-6-fluoropyridine. If any of the methyl groups are replaced by radicals, such as ethyl or butyl, which contain beta hyrogens, catalyst decomposition results. If a group, other than methyl, such as phenyl or benzyl—which do not contain beta hydrogens—is substituted for a methyl group, the rates of conversion of the alpha-chloropyridine reactants are greatly reduced.

Similarly, replacement of the chloride component of the catalyst by iodide or bromide results in a pronounced decrease in the reaction rate.

Since an increased reaction rate will result from the inclusion of any amount of tetramethyl ammonium or phosphonium chloride in the reaction mixture, the invention, in its broadest aspect, comprises carrying out the specified exchange reaction in the presence of any amount of catalyst sufficient to result in a detectable increase in the reaction rate. That is, at least a catalytically effective amount of the quaternary salt must be present in the reaction mixture. Advantageously, 0.1 mole or more of the catalyst per mole of the dihalopyridine reactant is employed, but the inclusion in the reaction mixture of more than the amount of the catalyst required to saturate the liquid phase is pointless and wasteful. Preferably, the catalyst is employed in an amount of from about 0.3 to about 0.6 mole per mole of the alpha-chloropyridine reactant.

It is of course possible to preform a solution of the corresponding quaternary ammonium fluoride by pre-reacting a quaternary ammonium halide with a fluoride source material. However, this is of no advantage as compared to in-situ generation of the quaternary fluoride, since equilibration between the chloride and fluoride salts will result and the reaction will stop unless some provision is made for selectively removing chloride ion from the liquid phase. When solid KF is present, chloride is removed across the solid/liquid interface as insoluble KCl, as a consequence of the exchange reaction betweek KF and the quaternary onium chloride.

Tetramethyl phosphonium chloride is very hygroscopic and therefore more difficult to work with than tetramethyl ammonium chloride. It is also poisonous. For these reasons, the quaternary ammonium catalyst is preferred.

The required intensity of stirring can be attained by any of several expedients well known to those skilled in the art. Exemplary of such expedients are baffling of reactor walls, higher rates of rotation of flat blade or propeller type impellers and use of high capacity centrifugal pumps for rapid slurry recirculation. As a general guide, an impeller rate of at least 50 rpm in a baffled reactor and of at least 300 rpm in an unbaffled reactor should be used. Usually, however, rates of at least 60 and 450 rpm are respectively preferred for baffled and unbaffled reactors. The ultimate limits on stirring rates are those imposed by such considerations as power requirements, inherent equipment limitations and cavitation tendencies. However, rates of about 100–150 and 550–650 rpm in baffled and unbaffled reactors respectively will usually be quite satisfactory. In any case, the stirring or pumping rate must be such that the distribution of the solid phase in the reaction mixture is essentially uniform, as defined earlier herein.

Suitable reaction temperatures range from about 100° to about 185° C. At temperatures substantially below 100°, the reaction rate is so low as generally to be uneconomic and at temperatures substantially above 180° C., catalyst and/or solvent stability becomes a serious problem. In fact, at temperatures of about 175° or more, it is essential to a full realization of the benefits of the present invention to provide a pad of a non-oxidizing or inert gas, such as nitrogen, for example, over the reaction mixture in the reaction vessel.

Pressure is not a critical parameter of the reaction and sub- or supra-atmospheric pressures may be employed. However, atmospheric or ambient pressures are most convenient and are accordingly preferred. If it is desired to operate at a temperature above the normal boiling point of the reaction mixture, it will of course be necessary to provide for operation under a pressure at least equal to the autogenous pressure of the reaction mixture.

In accordance with known principles, the contact time required to attain any desired conversion of the dihalopyridine reactant to 2,6-difluoropyridine will depend on the temperature, the concentrations of the reactants in the liquid phase, and the relative amounts of 2,6-dichloro- and 2-chloro-6-fluoropyridine present in the starting material. Rate constants, $k_1$ and $k_2$, for the successive reactions of 2,6-dichloro- and 2-chloro-6-fluoropyridine with fluoride at 150° C. in DMSO, using tetramethyl ammonium chloride as the catalyst, have been found to be 0.01378 and 0.00358 min.$^{-1}$, respectively. In contrast, the corresponding rate constants when no catalyst is employed are 0.00219 and 0.00060, respectively. When ethylene glycol is substituted for the quaternary salt catalyst, the constants drop to 0.00180 and 0.00050, respectively.

The following procedure was used in each of Examtion and are not to be construed as limiting the present invention to an extent not consistent with the claims appended to these specifications.

EXAMPLES

The following precedure was used in each of Examples 1 through 4, except as noted therein.

A 500 ml. 4-neck, round bottom flask was fitted with a thermometer, a size A glass stirring paddle powered by an air driven motor, a nitrogen gas inlet, a reflux condenser on which was mounted a drying tube, and a heating mantle. The current supply to the mantle was regulated by means of a Matheson LAB-STAT fitted to the thermometer.

The flask was charged with 230 ml (approximately 250 g) of Baker's reagent grade DMSO, dried over No. 4A molecular sieves, and the potassium fluoride (matheson, Coleman & Bell, Lot 5F05; 1.0 g mole). This mixture was stirred and heated until the temperature equilibrated at 150° C. The stirring speed was adjusted to about 400–500 rpm. 2.6-Dichloropyridine (0.25 g mole) and TMAC (tetramethyl ammonium chloride; 0.05 g moles; Aldrich) was charged into the reaction flask and a timer was activated. Aliquots (approximately 5 ml) were periodically withdrawn under a positive pressure of nitrogen gas. The aliquots were immediately quenched in a mixture of water (10 ml) and carbon tetrachloride solution was separated from the aqueous phase and placed in 1-dram vials with a drying agent (sodium sulfate). This solution was analyzed using a glpc (gas liquid partition chromatography) instrument, and the relative amounts of starting chlorinated pyridine, monofluoropyridine (intermediate), and difluorinated pyridine (product) were determined for each aliquot.

Rate constants for the formation of 2,6-difluoropyridine from the corresponding chloro compounds were estimated from the preceding amounts, using a computer program which assumed as its model two consecutive first-order reactions. The program was a non-linear parameter estimation routine (23) which was used to obtain the best least squared estimator of $k_1$ and $k_2$ from the data where $k_1$ and $k_2$ are first-order rate constants for the formation of monofluoro and difluoropyridines, respectively. The computations were done with an IBM 360 computer.

Half-life values ($t_{0.5}$) for $k_1$ may be reckoned by dividing $k_1$ into 0.693. Half-life values ($t_{0.5}$) and 95% completion values ($t_{0.95}$) may be estimated for $k_2$ by an iteration process (on a Hewlett Packard 9810A Calculator, for example) from the following equation (24).

$$y = \frac{k_2(1 - e^{-k_1 t}) - k_1(1 - e^{-k_2 t})}{k_2 - k_1}$$

where $y$ = the fraction of the reaction product.

EXAMPLE 1

The reaction, carried out as above described, was allowed to continue for a total of 1146.2 minutes (19.1 hours). A total of 10 aliquots were taken and analyzed, with the following results:

| | | Mole Percents | | |
|---|---|---|---|---|
| Aliquot No. | Elapsed Time | 2,6-Difluoro-Pyridine | 2-Chloro-6-fluoropyridine | 2,6-di-chloropyridine |
| 1 | 8.5 min. | 0.0 | 7.8 | 92.2 |
| 2 | 12.2" | 0.0 | 12.6 | 87.4 |
| 3 | 1.28 hrs. | 12.0 | 54.0 | 34.0 |
| 4 | 2.14 " | 22.7 | 60.8 | 16.5 |
| 5 | 3.70 " | 43.3 | 56.7 | 0.0 |
| 6 | 4.80 " | 54.1 | 45.9 | 0.0 |
| 7 | 10.06 " | 84.6 | 15.4 | 0.0 |
| 8 | 10.065 " | 85.3 | 14.7 | 0.0 |
| 9 | 19.03 " | 96.5 | 3.5 | 0.0 |
| 10 | 19.10 " | 96.7 | 3.5 | 0.0 |

$k_1$ and $k_2$, as above defined, were calculated to be 0.01378 and 0.00358, respectively.

EXAMPLE 2

Example 1 was essentially duplicated but with no TMAC or other catalyst present.

| Aliquot | Elapsed | Mole Percents | | |
|---|---|---|---|---|
| No. | Time | 2,6-$F_2$ | 2-Cl-6-F | 2,6-$Cl_2$ |
| 1 | 15.1 min. | 0.0 | 3.6 | 96.3 |
| 2 | 30.1 " | 0.0 | 6.2 | 93.8 |
| 3 | 58.9 " | 0.0 | 10.3 | 89.6 |
| 4 | 2.0 " | 4.4 | 18.9 | 76.6 |
| 5 | 2.98 hrs. | 4.9 | 27.2 | 67.8 |
| 6 | 3.92 " | 5.9 | 33.9 | 60.2 |
| 7 | 5.03 " | 7.5 | 40.6 | 51.9 |
| 8 | 6.14 " | 8.9 | 45.3 | 45.8 |
| 9 | 7.14 " | 10.6 | 49.4 | 40.0 |
| 10 | 21.54 " | 38.4 | 61.6 | 0.0 |
| 11 | 22.52 " | 40.5 | 59.5 | 0.0 |

$k_1 = 0.00211$
$k_2 = 0.00061$
(std. deviation = 0.000049)
(std. deviation = 0.000026)

The corresponding $k$ values obtained from a previous, essentially identical experiment were 0.00211 and 0.00061, respectively; the average values $k_1$ and $k_2$ were then 0.00219 and 0.00060.

EXAMPLE 3

Example 1 was essentially duplicated, but 0.05 g moles of benzyl trimethyl ammonium chloride, rather than TMAC, was used as the catalyst.

| Aliquot | Elapsed | Mole Percents | | |
|---|---|---|---|---|
| No. | Time | 2,6-$F_2$ | 2-Cl-6-F | 2,6-$Cl_2$ |
| 1 | 9.5 min. | 0.0 | 8.9 | 90.8 |
| 2 | 25.5 " | 3.6 | 24.1 | 70.9 |
| 3 | 58.0 " | 7.8 | 43.8 | 46.2 |
| 4 | 2.03 hrs. | 17.0 | 57.0 | 22.3 |
| 5 | 3.10 " | 26.7 | 57.5 | 10.6 |
| 6 | 4.15 " | 34.4 | 53.7 | 5.3 |
| 7 | 5.27 " | 42.7 | 49.2 | 5.2 |
| 8 | 6.40 " | 47.9 | 43.1 | 0.0 |
| 9 | 7.60 " | 51.6 | 38.3 | 0.0 |

$k_1 = 0.01145$
$k_2 = 0.00263$

Extra peaks found in the glpc scans of the aliquots were attributed to catalyst decomposition or interaction.

EXAMPLE 4

Example 1 was essentially duplicated, except that the only "catalyst" present in the reaction mixture was ethylene glycol; the glycol content was 0.05 gram moles, or 1.23% of the solvent weight (as compared to 1.2% of the solvent weight in Example 33 of British Pat. No. 1,306,517).

| Aliquot | Elapsed | Mole Percents | | |
|---|---|---|---|---|
| No. | Time | 2,6-$F_2$ | 2-Cl-6-F | 2,6-$Cl_2$ |
| 1 | 12.1 min. | — | — | — |
| 2 | 20.8 " | 0.0 | 3.8 | 96.2 |
| 3 | 45.3 " | 0.0 | 8.0 | 92.0 |
| 4 | 2.04 hrs. | 3.2 | 18.2 | 78.6 |
| 5 | 3.85 " | 4.5 | 30.2 | 65.2 |
| 6 | 5.88 " | 8.0 | 40.3 | 51.7 |
| 7 | 20.90 " | 28.8 | 59.3 | 12.0 |
| 8 | 24.33 " | 34.6 | 57.7 | 7.7 |
| 9 | 25.68 " | 36.1 | 57.4 | 6.5 |
| 10 | 28.77 " | 45.0 | 55.0 | 0.0 |

$k_1 = 0.00180$
$k_2 = 0.00050$

EXAMPLE 5

Attempted preparations of 2,6-difluoropyridine, by reaction of KF and 2,6-dichloropyridine in DMSO at 150° C., in which TMAC was replaced by tetraethyl- or tetrabutyl ammonium chloride, resulted in catalyst decomposition and little or no improvement over otherwise comparable, uncatalyzed reactions. When TMAC was replaced by phenyl trimethyl ammonium chloride, no catalytic effect was observable.

EXAMPLE 6

Example 1 was essentially duplicated, except that temperatures of 165° and 180°, with no inert gas pad, were employed in two runs and a third run was carried out at 180° with a nitrogen pad. The calculated rate constants are given below:

| Temperature | $N_2$ pad | $k_1$ | $k_2$ |
|---|---|---|---|
| 165° | No | 0.03259 | 0.00915 |
| 180° | Yes | 0.05953 | 0.00902 |
| (small amounts of several impurities formed) | | | |
| 180° | No | 0.06823 | 0.01538 |
| (from t = 0 to t = 50 minutes) | | | |

In the run made at 180° without an inert gas pad, the rate of conversion of 2,6-dichloropyridine dropped dramatically after about 30 minutes of contact. After a little more than 2 hours, a sulfurous odor, indicative of solvent decomposition, was noted and the condenser plugged with a white decomposition product after about 7 hours. At the time (~136 minutes) when dichloropyridine conversion was complete, the reaction product consisted of 60.5 mole percent 2-chloro-6-fluoropyridine and 39.5 mole percent 2,6-difluoropyridine. After 7 hours, the product composition was 50.4 mole % of the chloro/fluoro pyridine, 40.2 mole % difluoro and ~10 mole % impurities.

EXAMPLE 7

A run was carried out in a manner similar to Example 1, but with the following differences: temperatures, 240°; medium, sulfolane; product retention in reaction vessel, partial (reflux condenser mounted on Vigereaux column fitted with thermometer well, condensate take-off and condensate receiver). Aliquote for analysis were taken of the condensate accumulated in the receiver, as well as of the reaction vessel contents. The values calculated for $k_1$ and $k_2$ were 0.02505 and 0.00553, respectively. Since no detectable catalyst or solvent decomposition or interaction was noted, the relatively low values found for $k_1$ and $k_2$ may be attributed to the inferiority of sulfolane, as compared to DMSO, as a medium for the (catalyzed) reaction.

EXAMPLE 8

Example 1 was essentially repeated, except that tetramethyl phosphonium chloride (Orgmet Inc., Hampstead, New Hampshire) was employed as the catalyst. After 4 hours at 150°. the reaction product accounted for all of the dichloropyridine charged and consisted of 54.1 mole percent 2-chloro-6-fluoropyridine and 45.9 mole percent 2,6-difluoropyridine. After 7 hours, the product consisted of 33.5 mole percent of chlorofluoro compound and 66.5 mole percent of the difluoro compound. The values calculated for $k_1$ and $k_2$ were 0.01291 and 0.00351, respectively.

Although acids, as such, are not employed in the present process, the use of acid resistant materials of construction is recommended. Such materials are well known to practicing chemical engineers.

I claim:

1. The improvement in the process of preparing 2,6-difluoropyridine by reacting KF with an alpha-chloropyridine which is 2,6-dichloro- or 2-chloro-6-fluoropyridine, at an elevated temperature in an aprotic, polar solvent, whereby practical rates of conversion are attained without resort to temperatures in excess of about 185°, said improvement comprising:
 a. providing a mixture of solid KF particles and a solution in dimethyl sulfoxide of
  1. said alpha-chloropyridine reactant, and
  2. a catalytically effective amount of a catalyst which is $(CH_3)_4N^+Cl^-$, $(CH_3)_4P^+Cl^-$ or both;
  said mixture containing less than 0.1 gram of acids, bases or organic hydroxy compounds and less than about 1 gram of water, per 100 grams of dimethyl sulfoxide; and
 b. intensely stirring said mixture and maintaining the temperature thereof within the range of from about 100° to about 185°, the reaction being carried out under an inert atmosphere if a reaction temperature above about 180° is employed.

2. The process of claim 1 in which the catalyst is $(CH_3)_4N^+Cl^-$.

3. The process of claim 1 in which the reaction temperature is 180° C. or less.

4. The process of claim 3 in which the reaction temperature is within the range of from about 140° to about 175° C.

5. The process of claim 3 in which the reaction temperature is within the range of from about 145° to about 170° C.

6. The process of claim 3 in which the reaction temperature is within the range of from about 150° to about 165° C.

7. The process of claim 1 in which the amount of water present in the reaction mixture is less than 0.3 wt. percent of the amount of DMSO present therein.

8. The process of claim 1 in which the reaction is carried out in baffled vessel and a stirring rate of at least 50 rpm is maintained.

9. The process of claim 1 in which the reaction is carried out in an unbaffled and a stirring rate of at least 300 rpm is maintained.

10. The process of claim 9 in which a stirring rate of at least 450 rpm is maintained.

11. The process of claim 1 in which the reaction temperature is within the range of from about 145° to about 170° C., the reaction is carried out in baffled vessel and a stirring rate of at least 60 rpm is maintained.

12. The process of claim 1 in which the amount of KF introduced to the reaction mixture is from about 110 to about 125% of the stoichiometric requirement for the conversion to 2,6-difluoropyridine of the alpha-chloropyridine reactants charged to the reaction.

13. The process of claim 1 in which the alpha-chloropyridine is 2,6-dichloropyridine.

14. The process of claim 1 in which the reaction temperature is about about 175° and the reaction is carried out under an inert atmosphere.

15. The process of claim 1 in which the amount of said catalyst introduced to the reaction mixture is from about 0.3 to about 0.6 moles per mole of said alpha-chloropyridine reactants present therein.

16. The process of claim 1 in which the concentration of said alpha-chloropyridine reactant in said solution is from about 2 to about 3 moles per liter.

17. The process of claim 11 in which:
 1. the catalyst is $(CH_3)_4N^+Cl^-$, and the amount of it introduced to the reaction mixture is from about 0.3 to about 0.6 moles per mole of said alpha-chloropyridines present therein,
 2. the concentration of said alpha-chloropyridine reactant is from about 2 to about 3 moles per liter,
 3. the amount of KF introduced to the reaction mixture is from about 110 to about 125% of the stoichiometric requirement for conversion to 2,6-difluoropyridine of said alpha-chloropyridine, and
 4. the reaction mixture contains less than about 0.3 grams or less of water per 100 grams of DMSO.

* * * * *

UNITED STATES PATENT OFFICE
CERTIFICATE OF CORRECTION

PATENT NO. : 4,031,100
DATED : June 21, 1977
INVENTOR(S) : Thomas J. Giacobbe

It is certified that error appears in the above-identified patent and that said Letters Patent are hereby corrected as shown below:

Column 1, line 51, delete the last two letters "ed" from the word "decompositioned" ;

Column 3, line 55, the first word should be -- reacting -- instead of "reaction";

Column 7, line 54, delete "procedure was used in each of Exam-" and insert -- examples are for purposes of illustra-  -- ;

Column 8, line 14, insert after "tetrachloride" -- (5 ml), and the time was noted. The carbon tetrachloride -- ;

Column 12, line 22, (Claim 14) delete the first "about" and insert -- above -- .

Signed and Sealed this

Eighth Day of November 1977

[SEAL]

Attest:

RUTH C. MASON
Attesting Officer

LUTRELLE F. PARKER
Acting Commissioner of Patents and Trademarks